United States Patent
Shefsky

(10) Patent No.: US 7,623,614 B2
(45) Date of Patent: Nov. 24, 2009

(54) APPARATUS FOR INSPECTING OBJECTS USING CODED BEAM

(75) Inventor: Stephen I. Shefsky, Brooklyn, NY (US)

(73) Assignee: Thermo Niton Analyzers LLC, Billerica, MA (US)

( * ) Notice: Subject to any disclaimer, the term of this patent is extended or adjusted under 35 U.S.C. 154(b) by 99 days.

(21) Appl. No.: 11/923,532

(22) Filed: Oct. 24, 2007

(65) Prior Publication Data

US 2008/0095298 A1     Apr. 24, 2008

Related U.S. Application Data

(60) Provisional application No. 60/853,876, filed on Oct. 24, 2006.

(51) Int. Cl.
G01N 23/201 (2006.01)
G01N 23/203 (2006.01)

(52) U.S. Cl. ............................................. 378/2; 378/87

(58) Field of Classification Search ................... 378/2, 378/87; 250/363.06
See application file for complete search history.

(56) References Cited

U.S. PATENT DOCUMENTS

| | | | |
|---|---|---|---|
| 3,749,911 A * | 7/1973 | Hoover et al. ............... 378/146 |
| 4,209,780 A | 6/1980 | Fenimore et al. | |
| 4,241,404 A * | 12/1980 | Lux ............................... 378/2 |
| 4,360,797 A | 11/1982 | Fenimore et al. | |
| 4,389,633 A * | 6/1983 | Fenimore ................... 382/204 |
| 4,392,237 A | 7/1983 | Houston | |
| 4,506,374 A * | 3/1985 | Flynn ............................ 378/2 |
| 4,688,242 A | 8/1987 | Ema | |
| 5,606,165 A | 2/1997 | Chiou et al. | |
| 5,666,393 A | 9/1997 | Annis | |
| 5,930,314 A | 7/1999 | Lanza | |
| 5,940,468 A * | 8/1999 | Huang et al. ................... 378/57 |
| 6,192,104 B1 | 2/2001 | Adams et al. | |
| 6,205,195 B1 | 3/2001 | Lanza | |
| 6,269,142 B1 | 7/2001 | Smith | |
| 6,353,227 B1 * | 3/2002 | Boxen ..................... 250/363.1 |
| 6,453,007 B2 | 9/2002 | Adams et al. | |
| 6,737,652 B2 | 5/2004 | Lanza et al. | |
| 6,950,495 B2 | 9/2005 | Nelson et al. | |
| 7,136,453 B2 * | 11/2006 | Jupp et al. ..................... 378/87 |
| 2002/0031202 A1 | 3/2002 | Callerame et al. | |
| 2004/0218714 A1 | 11/2004 | Faust | |

OTHER PUBLICATIONS

Fenimore et al., "Coded Aperture Imaging with Uniformly Redundant Arrays," Applied Optics, vol. 17 ( No. 3), p. 337-347, (1978).

(Continued)

Primary Examiner—Edward J Glick
Assistant Examiner—Thomas R Artman
(74) Attorney, Agent, or Firm—Charles B. Katz

(57) ABSTRACT

An apparatus for inspecting objects utilizes a fan beam or flood beam to illuminate the inspected region of the object. A modulator, which may take the form of a movable mask, dynamically encodes the beam so that each segment of the inspected region receives varying amounts of radiation according to a predetermined temporal sequence. The resultant signal produced by a backscatter detector or optional transmission detector receiving radiation from the object is decoded to recover spatial information so that an image of the inspected region may be constructed.

25 Claims, 6 Drawing Sheets

OTHER PUBLICATIONS

Fenimore, E. E., "Coded Aperture Imaging: Predicted Performance of Uniformly Redundant Arrays," Applied Optics, vol. 17 (No. 22), p. 3562-3570, (1978).

Gottesman et al., "New Family of Binary Arrays for Coded Aperture Imaging," Applied Optics, vol. 28 (No. 20), p. 4344-4352, (1989).

* cited by examiner

APPARATUS FOR INSPECTING OBJECTS USING CODED BEAM

CROSS REFERENCE TO RELATED APPLICATION

This application claims the priority benefit under 35 U.S.C. §119(e) of U.S. Provisional Patent Application Ser. No. 60/853,876 entitled "Coded Beam Imaging System" and filed on Oct. 24, 2006, the entirety of which is incorporated herein by reference.

FIELD OF THE INVENTION

The present invention relates generally to the inspection of objects using an X-ray or other radiation beam, and more particularly to an apparatus and method for inspecting objects by illuminating the object with a coded radiation beam and detecting radiation scattered by and/or transmitted through the object.

BACKGROUND OF THE INVENTION

Scanning x-ray imaging systems are commonly used for the inspection of packages, luggage, cargo containers and vehicles. Commercially available scanning x-ray imaging systems can be broadly categorized into two types: flying-spot systems and line-scan systems. Flying-spot systems employ a "pencil" beam of radiation that is rapidly scanned over the object of interest. Such systems are capable of measuring either or both of transmitted and backscattered radiation. The pencil beam is formed by collimation (in two orthogonal dimensions), because practical methods for focusing x-rays of the required energy range are not available. Since the formation of the pencil beam excludes all but a tiny fraction (typically much less than one percent) of the available source flux, a flying-spot system requires a high power X-ray source to produce an image having acceptable resolution and signal-to-noise ratio.

Line scan systems utilize a "fan" beam of radiation to illuminate the object under inspection and a segmented detector to measure radiation transmitted through the object. Commercial line-scan systems, while advantageously using a much higher portion of the available source flux, are generally incapable of producing images from backscattered radiation, and hence their use is limited to applications where it is practical to position the radiation source and the detector on opposite sides of the inspected object and where detection of targets composed of light elements is not paramount.

The prior art contains several references that disclose x-ray imaging systems which attempt to take advantage of the relatively efficient source usage of line-scan systems while maintaining backscatter imaging capabilities. Representative examples of such references include U.S. Pat. No. 6,453,007 to Adams et al., which teaches a specially-shaped chopper wheel for rapidly alternating the illumination beam between fan and pencil shapes, and U.S. Pat. No. 6,269,142 to Smith, which teaches a line-scan imaging system adapted with a rotating beam stop that periodically interrupts the fan beam. In another approach, described in U.S. Patent Application Publication No. 2002/0031202 to Callerame et al., the inspected object is illuminated with a scanned set of pencil beams or a fan beam divided into sections, wherein each pencil beam or fan beam section is encoded by modulation with a unique characteristic frequency. In this manner, each simultaneously illuminated pixel-sized segment of an inspected area of the object may be associated with a different characteristic frequency in the detector signal, such that the detector signal may be demodulated (e.g., by using a filter bank) to recover spatial information and construct an image of the inspected region.

The method of coded aperture imaging is known in the art, and is has been used for gamma-ray and x-ray astronomy, radioactive materials management, nuclear medicine, and other applications involving non-focusable radiation. In a typical configuration, one or more radiation sources project a pattern through a coded mask onto a pixilated (segmented or otherwise position sensitive) radiation detector. An image of the source is then reconstructed from the projected pattern through a decoding algorithm. The coded aperture imaging method has the potential for improved sensitivity (relative to other known imaging methods such as "pinhole" imaging) by allowing radiation to arrive at the detector through a coded mask of large area and high openness (typically up to about 50% of the mask area). The mathematical techniques for encoding and decoding are well established, and are described, for example, in U.S. Pat. No. 4,209,780 to Fenimore et al., U.S. Pat. No. 5,606,165 to Chiou et al., and U.S. Pat. No. 6,737,652 to Lanza et al., as well as in Fenimore et al., "Coded Aperture Imaging With Uniformly Redundant Arrays," *Applied Optics*, 17(3): 337-347 (1978). A variety of encoding methods are available, including (without limitation) the following: uniformly redundant array (URA), modified uniformly redundant array (MURA), product array, m-sequence, pn-sequence and Hadamard difference set.

Straightforward application of traditional coded aperture imaging to neutron activated gamma-ray emission and to x-ray backscatter has been respectively proposed in U.S. Pat. No. 5,930,314 to Lanza and U.S. Patent Application Publication No. 2004/0218714 to Faust. Backscatter detection by the traditional coded aperture imaging method allows the source to flood the entire inspection area simultaneously for efficient use of the available source flux. For this method, pixilated detectors are required, and for high system performance these detectors must have large areas and fine segmentation.

Several variations on the traditional coded aperture imaging method have been described in the prior art. U.S. Pat. No. 5,940,468 to Huang et al. teaches the use of a fan beam to illuminate the inspected object, with plural large area coded masks interposed in the backscattered radiation path between the object and corresponding large-area detectors. This approach makes efficient use of the available source flux, but requires its large-area detectors to be finely segmented along one axis. U.S. Pat. No. 6,950,495 to Nelson et al. teaches a beam encoding scheme based on a wide-area radiation source in which the image of the inspected object is decoded from a series of backscatter responses to different source patterns. This scheme makes poor use of the available source flux because it requires the modulated source radiation to pass through a pinhole aperture en route to the inspected object. Furthermore, it is believed that the wide-area source required to implement the Nelson et al. scheme will be overly bulky, heavy, complex and expensive. Finally, U.S. Pat. No. 7,136,453 to Jupp et al. teaches a backscatter imaging system using a stationary coded mask with a source spot that moves over a planar area in a raster-scan manner. While this system generally makes efficient use of the available source flux and does not require segmented detectors, it is believed that a system of this general description would be prone to image distortion due to a number of factors, including, inter alia, backscatter from structures at the periphery of the scanned volume, variation of the path length from the source spot to any particular portion of the mask and any particular portion of the inspected object as the source spot is scanned, vignetting of the coded mask with variation of the source ray's angle of incidence, and parallax in the near field. Furthermore, the scanning x-ray source required by the Jupp et al. scheme would be difficult and expensive to implement.

Against the foregoing background, there remains a need in the art for an imaging apparatus that makes efficient use of available source flux, does not require segmented detectors, avoids or reduces the image distortion problems associated with prior art approaches, and is not prohibitively difficult or expensive to manufacture.

SUMMARY

Broadly described, an inspection apparatus configured in accordance with representative embodiment of the present invention includes a radiation source for generating a beam of illuminating radiation, a modulator positioned in the radiation beam path between the radiation source and the inspected object, at least one detector positioned to receive radiation emanating from an inspected region of the object, and a processor for processing a series of signals produced by the at least one detector to generate an image of the inspected area. The modulator is operable to spatially modulate the beam in a nonharmonic dynamic (time-varying) manner, such that each pixel-sized segment of the inspected region receives varying amounts of radiation according to a predetermined temporal sequence selected to allow recovery of information regarding the position of the segment. As used herein, the term "nonharmonic" denotes that the temporal illumination sequence of each segment does not need to have a unique characteristic frequency associated therewith.

In accordance with a more specific embodiment of the inspection apparatus, the radiation source is a fixed position x-ray tube, collimated to form a fixed fan-beam profile. The modulator takes the form of a movable mask, typically in the form of a rotating wheel or barrel, positioned in the fan beam. The movable mask has a one-dimensional encoding array consisting of a pattern of holes or slots such that at any particular mask position the fan beam will itself be broken into a predetermined pattern of discrete "on" and "off" sectors. In certain embodiments, the encoding array may correspond to one or a series of uniformly redundant arrays or modified uniformly redundant arrays. An optional transmission detector intercepts the plane of the fan beam on the opposite side of the inspection subject. One or more unsegmented detectors intercept backscatter radiation from the inspected object. As the mask is shifted from position to position, the detectors measure changing radiation signals that reveal spatial variations of the density and composition of the object. Signals from the detectors are recorded for at least one encoding array length of the movable mask, and are then digitally processed to decode a single scan line each of the optional transmission image and of the backscatter image. As the inspection object is moved in small increments in a direction perpendicular to the plane of the fan beam, additional scan lines of the image are thus acquired and processed until the full image is obtained.

In accordance with another specific embodiment of inspection apparatus, the fixed position radiation source is collimated to form a flood beam having wide angular dispersion in two dimensions. A mask having a two-dimensional encoding array, which may be either flat or formed as a cylinder, is interposed in the flood beam between the source and the inspected object. The mask is movable in two dimensions such that during the course of an inspection the mask can be translated (that is, raster-scanned) and/or rotated through a full set of complementary mask positions. An optional transmission detector intercepts the flood beam on the opposite side of the inspection subject, and one or more unsegmented detectors intercept backscatter radiation from the object. As the coded mask is shifted through its various positions, signals from the detectors are recorded. The inspection subject remains stationary (relative to the imaging system) during the recording process. The recorded signals are then processed digitally to decode the optional transmission and backscatter images. In a variation of this embodiment, the two-dimensional coded mask is designed to produce a full set of complementary mask positions by translating or rotating the said mask in a single dimension. The coded mask may be advanced from position to position in discrete increments or by way of uniform continuous motion.

Embodiments of the present invention have the advantages of compatibility with backscatter and transmission imaging using unsegmented detectors, and efficient use of the available source flux. Other features and advantages of the invention may become apparent upon review of the detailed description set forth below and the accompanying drawings.

DETAILED DESCRIPTION OF EMBODIMENTS

Figure 1:
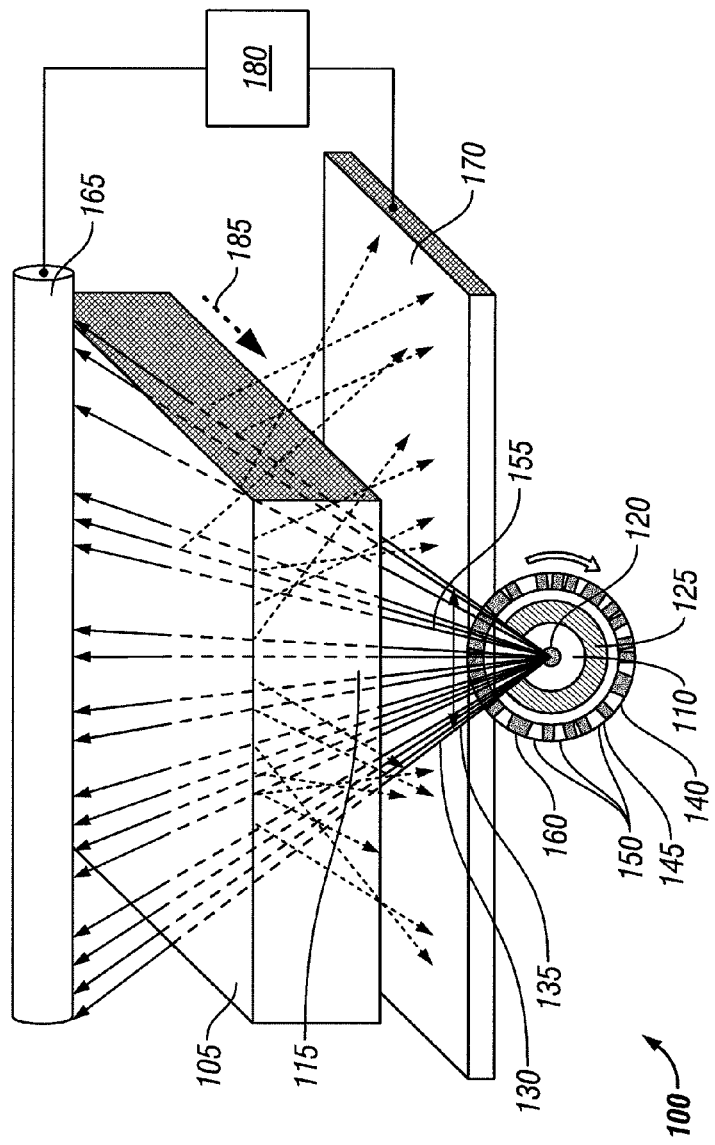
FIG. 1 is a symbolic diagram of an apparatus for inspecting objects configured in accordance with a first embodiment of the invention, wherein the inspected object is illuminated with a modulated fan beam.

FIG. 1 is a symbolic diagram of an apparatus 100 for inspecting an object 105 configured according to a first illustrative embodiment of the invention. A radiation source 110 positioned to illuminate an inspected region 115 of object 105 may take the form of a fixed position x-ray tube 120, capable of focusing the electron anode spot to a sufficiently small diameter to meet the image resolution requirement, positioned within stationary beam collimator 125. This arrangement of x-ray tube 120 and collimator 125 forms a fan beam 130 of radiation having narrow angular dispersion in one transverse axis (perpendicular to the plane of the figure) and a broad angular dispersion (typically 45 to 90 degrees) in the other transverse axis 135. Fan beam 130 defines a plane transverse to the direction of movement of object 105 during the image construction process, as discussed below.

Fan beam 130 is spatially and temporally modulated by a modulator 140 positioned in the beam path. Modulator 140 may be implemented as a movable mask 145, constructed from a suitable material and to an appropriate thickness that is substantially opaque at the wavelength(s) emitted by radiation source 110, such that portions of fan beam 130 striking the intact areas of mask 145 are blocked from illuminating corresponding segments of object 105 (as used herein, the term "segment" denotes a discrete area forming a part of the inspected region of object 105). Mask 145 is adapted with a series of apertures or transmissive windows 150 that allow several discrete sectors 155 of the fan beam to emerge and illuminate corresponding segments of inspected region 115 of object 105 at any given position of mask 145. As will be further discussed hereinbelow, apertures 150 are arranged and sized to define (in connection with the adjacent opaque areas of mask 145) a one-dimensional encoding array 160. In a typical implementation, encoding array 160 has an open area of approximately 50%, so that about half of the total fan beam flux is available to illuminate object 105 at any position of mask 145. An optional transmission detector 165, which may be segmented or unsegmented, intersects the plane of fan beam on the opposite side of object 105. At least one unsegmented backscatter detector 170 is placed on the near side of object 105 to receive radiation backscattered from object 105. As used herein, backscatter radiation is considered to include source radiation scattered by the inspected object 105 both incoherently (as Compton scatter) and coherently (as Rayleigh scatter), as well as x-ray fluorescence (XRF) of atoms in the inspection subject excited by the source radiation, and so backscatter detector 170 may detect one or more of these types of backscattered radiation. Backscatter detector 170 and optional transmission detector 165 convey signals representative of the intensity of the received radiation to processor 180, which processes the signals to construct an image of the inspected region 115. Backscatter detector 170 is preferably configured with as large an active detection area as practical so that a large fraction of the backscattered radiation may be detected. Certain implementations of the invention may utilize an array comprising two or more unsegmented backscatter detectors; however, in contradistinction to prior art approaches utilizing segmented backscatter detectors, the spatial resolution of the image of the inspected object is not determined by the size and/or number of the backscatter detectors.

Figure 2:
FIG. 2 is an example of a one-dimensional encoding pattern.

Mask 145 may be configured as a cylinder (or other continuous surface, such as loop or chain) having a central axis around which the mask is shifted (indexed) in a sequence of discrete rotational positions. Alternatively, mask 145 may be rotated in a continuous (non-indexed) manner. As shown, mask 145 may be controllably rotated by any suitable transport mechanism (not depicted), such as a stepper or voice-coil motor in mechanical association with the mask. Alternatively, mask 145 may take a planar shape, in which case it is progressively shifted by a suitable transport mechanism parallel to axis 135 in a sequence of discrete translational positions. The pattern of apertures 150 in mask 145 follows a sequence selected to obtain satisfactory image resolution and signal-to-noise ratio. The prior art (see, e.g., Gottesman et al., "New Family of Binary Arrays for Coded Aperture Imaging," *Applied Optics*, 28(20): 4344-4352 (1989), the entirety of which is incorporated by reference) details techniques for generating one-dimensional and two-dimensional uniform redundant arrays (URA) and modified uniform redundant array (MURA) that have optimal properties for coded aperture imaging applications, including a high fraction of open area (approximately 50% of the total area) and a decoding function that is "unimodular", yielding a uniform noise response across the image field. FIG. 2 depicts an example of an encoding array 160 consisting of a set of apertures 150 arranged in a linear MURA pattern of length 37. Masks having URA and MURA patterns also have the property that cyclic shifts of the mask pattern preserve the uniform response. The aforementioned Gottesman et al. reference also explains how to generate the decoding function associated with each URA or MURA, and how to apply the decoding function to the encoded data to produce an image. Other methods that may be employed to generate suitable one-dimensional and/or two-dimensional encoding arrays include product array, m-sequence, pn-sequence, and Hadamard difference set, all of which are described in detail in the prior art.

Mask 145 is positioned and sized such that encoding array 160 or a cyclic shift of the encoding array modulates fan beam 130 at any instant. The length of encoding array 160 must match or exceed the extent of the arc of fan beam 130 at modulator 140. The full rotation of a cylindrical mask (such as mask 145) or the fall translational shift of a planar mask may include one or several repeats of the encoding array pattern, but not more than one array length of the mask may be allowed to encode the usable portion of fan beam 130 at any one position of mask 145.

Figure 3A:
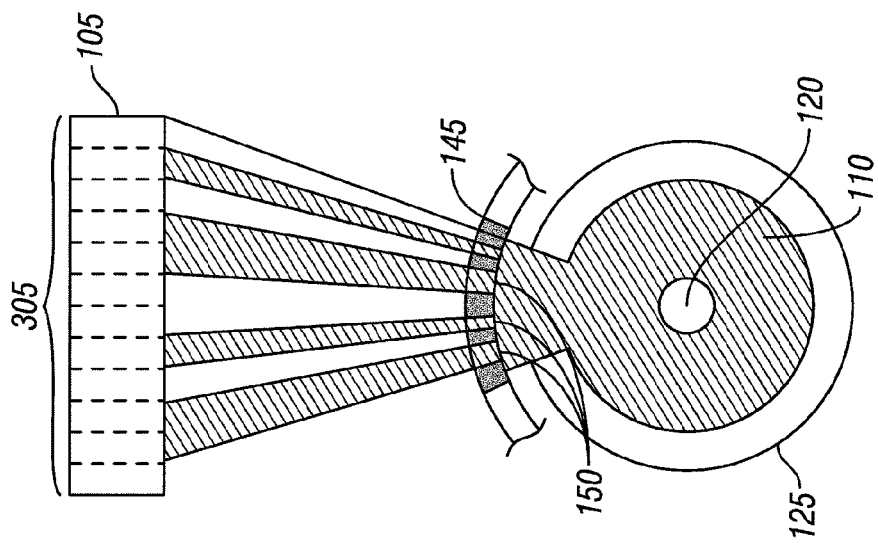
FIGS. 3A and 3B are symbolic diagrams illustrating the effect of shifting the mask position on the illumination of the inspected region of the object.
Figure 3B:
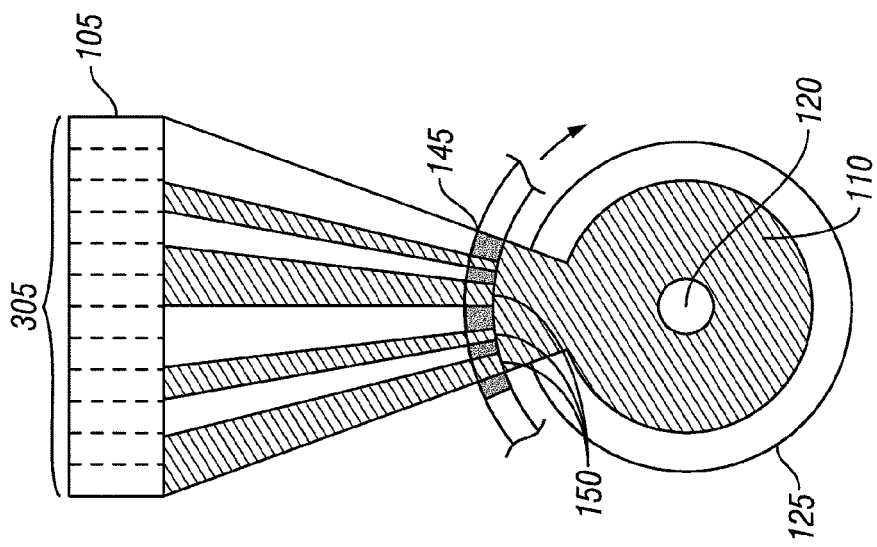

As mask 145 moves, encoding array 160 modulates fan beam 130 in a cyclical manner, such that the several segments of the inspected region of object 105 receive varying amounts of radiation according to the encoding sequence. It is noted that a segment in spatial correspondence to a blocked (intact) region of mask 145 may receive a small amount (relative to the amount received when it is in correspondence to an aperture 150) of spurious radiation transmitted through apertures 150 adjacent to the blocked region or reflected or scattered from other surfaces of apparatus 100. The effect of the movement of mask 145 is illustrated by FIGS. 3A and 3B. FIG. 3A depicts the illumination pattern projected on segments 305 of an inspected region of object 105 (which, in this case, constitutes a narrow band defined by the intersection of the full fan beam 130 with object 105) when mask 145 is at an initial rotational position. When mask 145 is rotationally shifted by one position, as shown in FIG. 3B, the illumination pattern is advanced in the direction of rotation. Each segment of the inspected region of object 105 receives the encoding sequence of illumination with a phase shift corresponding to the position of mask 145 relative to the segment. As each segment receives varying amount of radiation in accordance with the encoding sequence, radiation emanating from object 105 (e.g., backscattered and/or transmitted radiation) strikes backscatter detector 170 and optional transmission detector 165, which generate signals representative of the intensities of the received radiation. The detector responses are recorded for at least one full cycle of the mask movement, and then processor 180 applies the appropriate decoding function to each detector's temporal response to generate an image of the inspected region (i.e., a line scan). Object 105 is then advanced (e.g., by a conveyor) in the direction indicated by arrow 185 to a new position relative to the plane of fan beam 130 in order to acquire an image of an adjacent region (line scan) of object 105. The several steps of alternating illumination, detection, recording, decoding, and advancement of object 105 are repeatedly performed until the complete image of object 105 is constructed. This image may, for example, be displayed on a monitor for real-time viewing by an operator, or stored for later review and analysis.

It should be understood that, in contradistinction to the approach described in the aforementioned Callerame et al. reference, embodiments of the present invention do not depend on the use of spatially varying illumination sequences having unique characteristic frequencies in order to recover spatial information from the detector signal. In fact, the sequences in which different segments 305 receive illumination may (and typically will) share a number of the same frequencies. In this manner, modulator 140 may be considered to provide nonharmonic modulation of beam 130.

Figure 4:
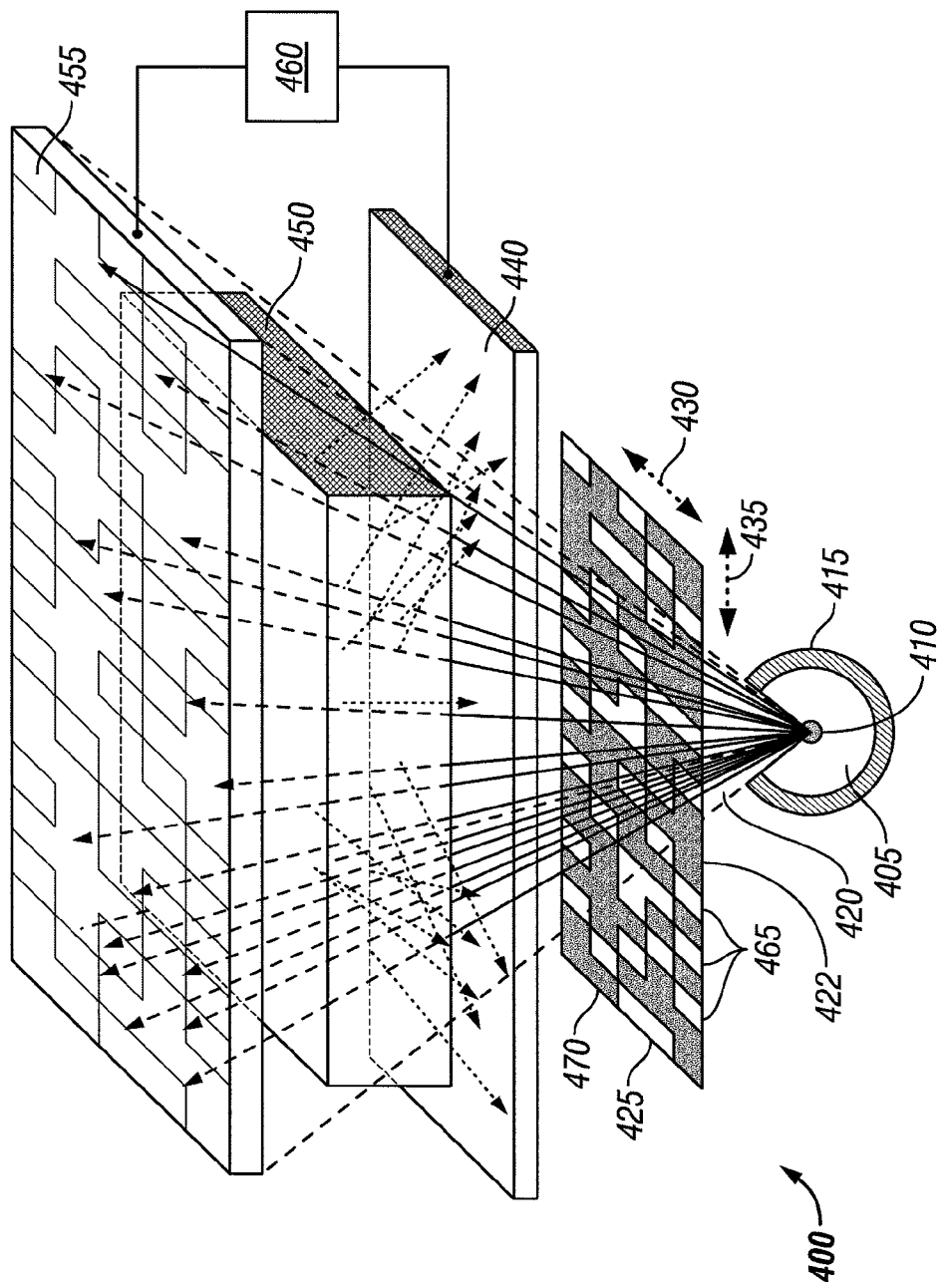
FIG. 4 is a symbolic diagram of an apparatus for inspecting objects configured in accordance with a second embodiment of the invention, wherein the inspected object is illuminated with a modulated flood beam.

FIG. 4 depicts an inspection apparatus 400 constructed in accordance with a second embodiment, which employs a "flood" beam (i.e., an illuminating beam expanded in two orthogonal transverse dimensions) rather than the fan beam described in connection with the FIG. 1 embodiment, and thereby utilizes a substantially greater fraction of the source's available flux. In this embodiment, radiation source 405 is provided having an x-ray tube 410 and a collimator 415 arranged around x-ray tube 410 to allow radiation to be emitted as a flood beam 420 with broad angular dispersion in two transverse dimensions. Flood beam 420 passes through a modulator 422, comprising a two-dimensional mask 425 which can be translated in two orthogonal axes 430 and 435 (using, for example, one or more stepper motors in mechanical association with mask 425) to obtain the full complement of beam patterns required to encode the image. In an alternative implementation, mask 425 may be formed as a cylinder, and the illumination sequence is effected by both rotating and translating the mask. At least one unsegmented backscatter detector 440 is positioned to receive radiation scattered from object 450. An optional transmission detector 455, which may be segmented or unsegmented, is positioned to receive radiation transmitted through object 450. In order to produce a full transmission image, optional transmission detector 455 should be sufficiently large to intercept the full flood beam (noting, however, that a smaller detector may be employed if forward-scattered or forward-emitted radiation rather than transmitted radiation is to be detected). Backscatter detector 440 and optional transmission detector 455 convey signals representative of the intensity of the received radiation to processor 460, which processes the signals to construct a two-dimensional image of the inspected region. If the dimensions of flood beam 420 at its intersection with object 450 exceed the corresponding dimensions of object 450 (i.e., if the inspected region encompasses the entirety of object 450), then the full image of object 450 may be acquired while object 450 is held stationary; otherwise, the fall image may be constructed by generating several partial images each acquired while object 450 is held at a different position relative to flood beam 420 so as to scan the (two-dimensional) inspected region over the full extent of object 450, and then stitching the partial images together to produce a full image. The sequence of illumination, detection, recording of the detector responses, and decoding of the two-dimensional image (and, if necessary, repositioning of the object relative to the beam) proceeds in a manner closely analogous to the sequence by which an image is acquired employing the fan beam system described above in connection with FIG. 1. As in the FIG. 1 embodiment, modulator 422 provides nonharmonic modulation of beam 420, since apparatus 400 does not rely on the use of spatially varying illumination sequences having unique characteristic frequencies in order to recover spatial information from the detector signal.

Figure 5:
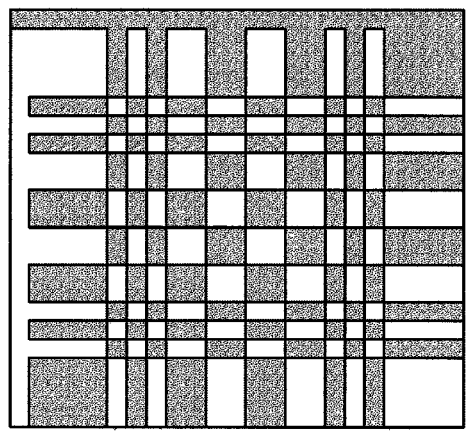
FIG. 5 is an example of a two-dimensional encoding pattern.
Figure 6:
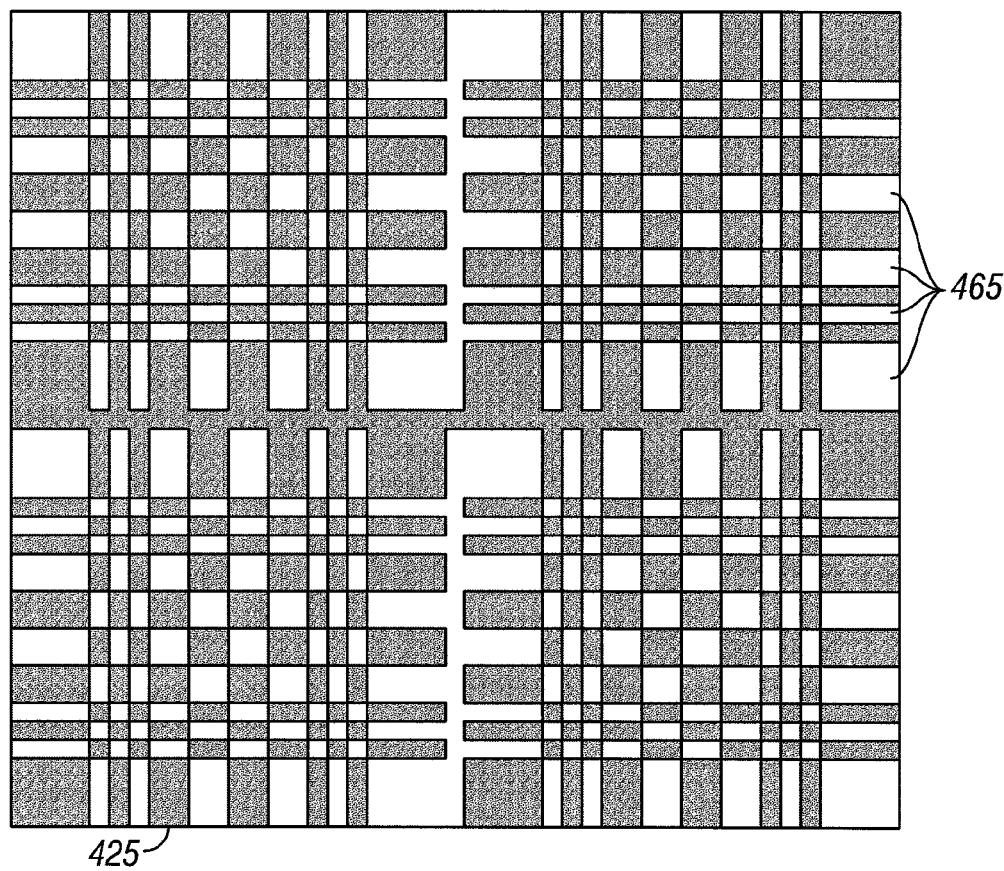
FIG. 6 depicts a two-dimensional mask using the encoding pattern of FIG. 5 to allow for full overlap for translating the mask in two orthogonal dimensions.

Mask 425 is adapted with a pattern of apertures or transmissive windows 465 defining a two-dimensional encoding array 470. Encoding array 470 may be generated according to the square MURA scheme described by the aforementioned Gottesman et al. reference. An example of an encoding pattern produced by the square MURA scheme is shown in FIG. 5. In such a case, the movable mask must be large enough to cover the array area plus full overlaps in each of the two translation dimensions. Therefore, the mask has about four times the area of the array. FIG. 6 depicts a mask 425 designed in this manner based on the encoding pattern of FIG. 5.

Figure 7:
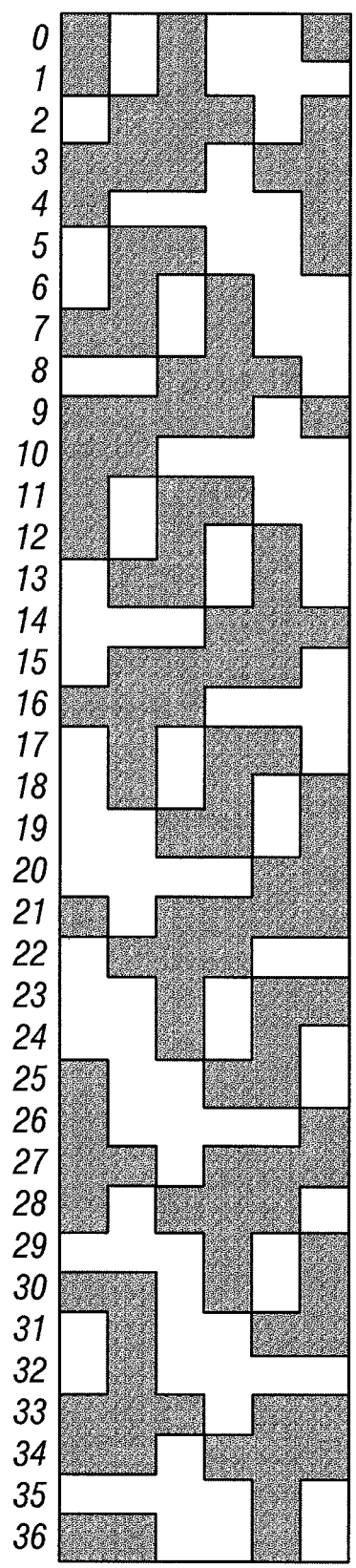
FIG. 7 is an example of a two-dimensional encoding pattern of a scrolling type.

A variation on the FIG. 4 inspection apparatus utilizes a two-dimensional mask that has been designed to be translated or rotated in only one direction. FIG. 7 shows an encoding pattern of the scrolling type for a 6×6 pixel array that may be configured as a two dimensional mask in the form of a flat rectangle, a continuous band, or a flat disk. An encoding pattern of the scrolling type for an m by n pixel image array may be constructed from an encoding sequence of length l where l is greater than m*n and is relatively prime to the array width m. The encoding sequence of length l may be a linear URA or linear MURA as described in the aforementioned Gottesman et al. reference (FIG. 2 depicts an encoding pattern of this type) or any of a number of binary sequences having the requisite properties that the set of l unique cyclic permutations of the binary sequence determines an l by l matrix which can be inverted, and which inverse matrix (the decoding matrix) is unimodular—all of its elements have identical magnitude and differ only in sign. Such binary sequences may be derived from quadratic residue sets, Hadamard difference sets, cyclic difference sets, twin-prime sets, or pseudo-noise sequences. The encoding pattern is formed by applying the encoding sequence of length l repeatedly across the scroll width m, and wrapping around to the beginning of the next line as necessary, for a total of l lines. The full mask pattern then has the dimensions of m*l. If the mask does not wrap from the end to the start like a continuous band, then the first (n−1) rows must be repeated at the end of the pattern to accommodate overlap.

Figure 8:
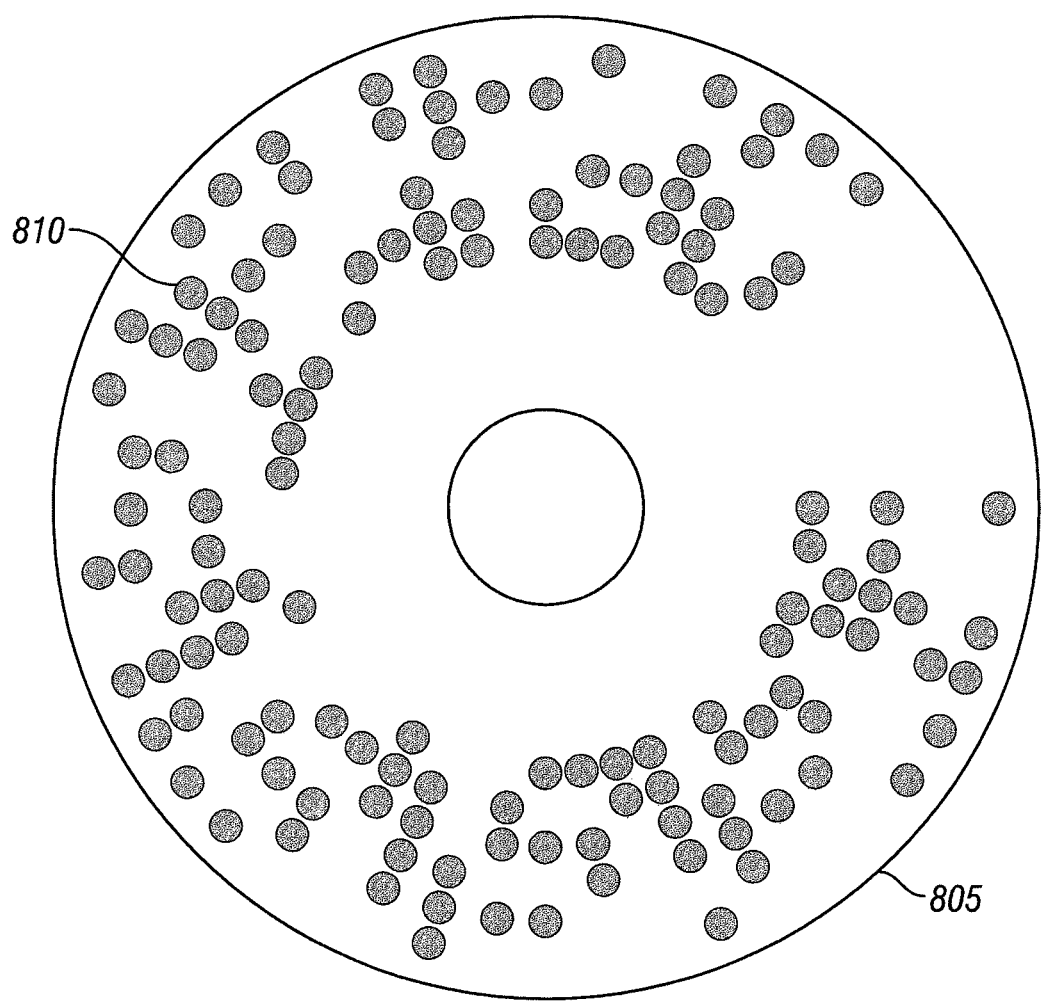
FIG. 8 depicts a disk-shaped rotatable mask using the encoding pattern of FIG. 7.

FIG. 8 shows a design for a disk-shaped mask 805 using an encoding pattern of the scrolling type for a 6×6 pixel sector-shaped image array. Each aperture 810 is sized, shaped and arranged such that for certain discrete increments of the mask's rotation the hole coordinates align with a predetermined grid. In this particular design, all apertures 810 are identical in size and shape.

A mask designed to translate or rotate in a single direction facilitates mask motion that is continuous rather than incremental. Continuous mask motion combined with continuous operation of the radiation source and detector will naturally lead to a degree of image blurring along the direction of motion. Operation of the radiation source in discrete pulses or bursts synchronized with the mask advancement can reduce or eliminate the blurring effect. Alternately, the detector may be gated on and off in a manner synchronous with the mask advancement.

It will be appreciated that the coded aperture imaging technique employed by embodiments of the present invention represents a significant improvement of signal-to-noise ratio (SNR) relative to alternative imaging techniques. Fenimore ("Coded Aperture Imaging: Predicted Performance of Uniformly Redundant Arrays", *Applied Optics*, 17(22): 3562-3570 (1978)) presents a formula for calculating the improvement of SNR (the "multiplexing advantage") of a URA-based coded aperture system over a pinhole camera system of equivalent resolution. The same formula describes the multiplexing advantage of a MURA or URA-based coded beam system over a flying spot system of equivalent resolution and source intensity.

The foregoing embodiments are presented by way of non-limiting examples. It should be noted that the invention embraces many possible modifications to and variations on the disclosed embodiments. For example, although the disclosed embodiments utilize a beam of x-rays to interrogate the inspected object, alternative implementations may utilize radiation located elsewhere in the electromagnetic spectrum (e.g., gamma rays, UV radiation, visible light), particle beams (e.g., a neutron beam), or even an ultrasonic or acoustic beam. Furthermore, the beam may be spatially and temporally modulated by any suitable device or combination of devices in place of the moving mask arrangement disclosed above. In one example, the modulator may take the form of a one-dimensional or two-dimensional array of shuttered apertures, whereby each aperture has a shutter associated therewith that is programmed to open and close in accordance with a specified sequence. According to another example, the mask may be replaced with a structure having a pattern constructed from elements of a radiation reflecting medium (for example, pyrolytic graphite) to obtain a coded beam. In such a design, the encoding pattern for a reflecting medium is merely the complement of an encoding pattern for a mask. In yet another implementation, the modulator may take the form of a cylindrical drum-like structure rotatable about a central axis, the drum having a series of surfaces of reflecting and non-reflecting material extending generally parallel to the central axis.

For certain types of illuminating beams, it may be advantageous to integrate the modulator with the radiation source. In one example of such an integrated structure, the source/modulator may take the form of an array of radiation emitters, the output of each emitter being independently modulated (in a manner similar to an LED projector) so that the resultant composite beam has a prescribed spatial distribution at any given time.

According to another implementation of the present invention, the collimator structures for forming the radiation beam may be placed between the modulator (e.g., a movable mask) and the inspected object, rather than (as depicted in FIGS. 1 and 4) between the x-ray tube and the modulator.

As noted above, the term "backscatter radiation" is intended to include source radiation scattered by the inspected object both incoherently (as Compton scatter) and coherently (as Rayleigh scatter), as well as x-ray fluorescence (XRF) of atoms in the inspected object excited by the source radiation. If the backscatter detectors are equipped with energy dispersive capability or energy selective filtration, it is in principle possible to selectively image a specific chemical element or a set of elements in or on the surface of the inspected object. The method of encoding the source illumination with a movable coded mask and subsequently decoding an image from the detected signal remains identical for such an imaging XRF system as for the coded beam inspection systems described above. It is further noted that, in certain embodiments of the invention, one or more detectors may be arranged on the far side of the object (i.e., on the side opposite from the source and modulator) to receive and detect radiation scattered from the inspected object (which is defined as including radiation emitted from the object via XRF) in a forward direction. A detector of this description may also be equipped with energy dispersive capability or energy selective filtration in order to selectively image a specific chemical element or a set of elements in or on the surface of the inspected object.

In certain implementations, it may be desirable to combine two or more components of the inspection apparatus in a common enclosure in order to reduce the size of the apparatus and provide for in situ inspection of objects of interest, such as vehicles or shipping containers. In one example, a portable inspection apparatus may be constructed by integrating the source, modulator, detector and processor components into a single housing.

It is to be generally understood that while the invention has been described in conjunction with the detailed description of certain illustrative embodiments, the foregoing description is intended to illustrate and not limit the scope of the invention, which is defined by the scope of the appended claims. Other aspects, advantages, and modifications are within the scope of the following claims.

What is claimed is:

1. Apparatus for inspecting an object, comprising:
   a radiation source for generating an illuminating beam expanded along at least one transverse dimension;
   a modulator, disposed in the illuminating beam path between the radiation source and the object, for spatially modulating the illuminating beam in a nonharmonic time-varying manner, such that each segment of an inspected region of the object receives varying amounts of radiation according to a predetermined temporal sequence;
   at least one detector positioned to receive at least one of backscattered radiation and forward-scattered radiation emanating from the object in response to impingement of the illuminating beam on the inspected region; and
   a processor, coupled to the at least one detector, for processing a sequence of signals generated by the at least one detector to construct an image of the inspected region.

2. The apparatus of claim 1, wherein the modulator comprises a mask having an encoding array of transparent and opaque areas, and a transport mechanism for repeatedly shifting or continuously moving the encoding array relative to the illuminating beam.

3. The apparatus of claim 2, wherein the encoding array is a one-dimensional array.

4. The apparatus of claim 3, wherein the mask is formed as a continuous surface, and the transport mechanism is configured to rotate the mask about the radiation source.

5. The apparatus of claim 2, wherein the encoding array is a two-dimensional array.

6. The apparatus of claim 5, wherein the transport mechanism is configured to perform one of: translating the mask in first and second axes substantially transverse to the axis of propagation of the illuminating beam, or translating and rotating the mask.

7. The apparatus of claim 5, wherein the encoding array is circumferentially disposed about the mask, and the transport mechanism is configured to rotate the mask.

8. The apparatus of claim 2, wherein the encoding array comprises one or a series of uniformly redundant arrays or modified uniformly redundant arrays.

9. The apparatus of claim 2, wherein the sum of the transparent areas is approximately fifty percent of the total area of the encoding array.

10. The apparatus of claim 1, wherein the illuminating beam is a fan beam expanded along a first dimension.

11. The apparatus of claim 10, further comprising a conveyor for moving the object in a direction generally orthogonal to the first dimension, such that the inspected region is progressively scanned over the object or a portion of interest thereof.

12. The apparatus of claim 1, wherein the illuminating beam is a flood beam expanded along first and second dimensions.

13. The apparatus of claim 1, wherein the illuminating beam is an electromagnetic radiation beam.

14. The apparatus of claim 13, wherein the illuminating beam is an X-ray beam.

15. The apparatus of claim 1, wherein the illuminating beam is a particle beam.

16. The apparatus of claim 1, wherein the at least one detector is positioned to receive radiation backscattered by the object.

17. The apparatus of claim 1, wherein the at least one detector is positioned to receive forward-scattered radiation.

18. The apparatus of claim 16, wherein the at least one detector comprises an energy dispersive detector, and the processor is configured to constrnct an image of the distribution of a specified element or set of specified elements in the object.

19. The apparatus of claim 16, wherein the at least one detector is configured to preferentially select radiation characteristic of a selected set of specified elements.

20. The apparatus of claim 1, wherein the modulator comprises a movable surface having disposed thereon an encoding array defined by a pattern of reflecting and non-reflecting material.

21. A method of inspecting an object, comprising steps of:
generating an illuminating beam expanded along at least one transverse dimension;
spatially modulating the illuminating beam in a nonharmonic time-varying manner, such that each segment of an inspected region of the object receives varying amounts of radiation according to a predetermined temporal sequence;
receiving at a detector at least one of backscattered or forward-scattered radiation emanating from the object in response to impingement of the illumination beam on the inspected region and generating a sequence of signals representative of the intensity of the received radiation; and
processing the sequence of signals to construct an image of the inspected region.

22. The method of claim 21, wherein the step of spatially modulating the beam comprises repeatedly shifting or continuously moving relative to the illuminating beam a mask having an encoding array of transparent and opaque areas.

23. The method of claim 21, further comprising a step of repeatedly moving the object, such that the inspected region is progressively scanned over the object or a portion of interest thereof.

24. The method of claim 21, wherein the step of receiving radiation comprises receiving radiation fluoresced by the object.

25. The method of claim 24, wherein the step of processing the sequence of signals includes identifying radiation having one or more wavelengths or energies characteristic of a specified element or set of specified elements, and constructing an image of the distribution of the specified element or set of specified elements in the object.

* * * * *